United States Patent [19]
Plotkin et al.

[11] 4,334,017
[45] Jun. 8, 1982

[54] METHOD FOR DETECTING CANCER IN MAMMALIAN TISSUE

[75] Inventors: George M. Plotkin, Lynn; George Wolf, Lexington, both of Mass.

[73] Assignee: Massachusetts Institute of Technology, Cambridge, Mass.

[21] Appl. No.: 243,860

[22] Filed: Mar. 16, 1981

Related U.S. Application Data

[63] Continuation-in-part of Ser. No. 30,182, Apr. 16, 1979, abandoned.

[51] Int. Cl.$^3$ ............... G01N 33/54; C12Q 1/54; C12Q 1/48
[52] U.S. Cl. .................. 435/7; 435/14; 435/15; 435/808; 424/8; 424/12; 23/230 B
[58] Field of Search .............. 23/230 B; 435/4, 6, 435/7, 14, 15, 16, 172, 808; 424/1, 2, 7, 8, 12

[56] References Cited

U.S. PATENT DOCUMENTS

| | | | |
|---|---|---|---|
| 3,558,435 | 1/1971 | Rey | 435/14 |
| 3,616,254 | 10/1971 | Beutler | 435/15 |
| 4,087,331 | 5/1978 | Bucolo | 435/15 |
| 4,132,600 | 1/1979 | Plotkin | 435/14 |

OTHER PUBLICATIONS

Plotkins et al., "Uridine 5′-Diphosphate Galactose:"-Glycoprotein Galactosyl Transferase Activity in Exfoliated Bladder Epithelial Cells in Rats fed N-14-(5-Nitro-2-Furyl)-2-Thiazolyl)Formamide", Cancer Biochem. Biophys., 1977, vol. 2, pp. 59-63.
Freilich et al., "A Micro Method for Simultaneous Determination of Galactosyltransferase and 5′ Nucleotidase Activities in Cell Fractions", Biochem. J. (1975), pp. 741-743.
Chemical Abstracts, vol. 83: 55028j (1975).
Chemical Abstracts, vol. 87: 113667(m) (1977).
Chemical Abstracts, vol. 90: 134341d (1979).
Chemical Abstracts, vol. 86: 51979j (1977).
Chemical Abstracts, vol. 80: 130989(s) (1974).
Chemical Abstracts, vol. 88: 185747g (1978).

Primary Examiner—Ernest G. Therkorn
Attorney, Agent, or Firm—Arthur A. Smith, Jr.; David E. Brook

[57] ABSTRACT

An improved method for assaying for cancer by detecting β-linked galactose moieties associated with cells is disclosed wherein a label specific for such moieties is added to the cells and subsequently sensed.

12 Claims, No Drawings

METHOD FOR DETECTING CANCER IN MAMMALIAN TISSUE

RELATED APPLICATIONS

This is a continuation-in-part of Ser. No. 030,182, filed Apr. 16, 1979, now abandoned.

TECHNICAL FIELD

This invention is in the field of biochemistry.

BACKGROUND ART

It has been shown that exfoliated bladder cells obtained from the urines of rats fed N-[4-(5-nitro-2-furyl)-2-thiazolyl]formamide (FANFT) for sufficient periods to produce bladder cancer contained significantly increased amounts of the enzyme galactosyl transferase. See Plotkin, G. M., Brigham, S. C., Wolf, G., Jacobs, J. B. and Arai, M., "Uridine 5'-diphosphate galactose:-glycoprotein galactosyl transferase activity in exfoliated bladder epithelial cells in rats fed N-[4-(5-nitro-2-furyl)-2-thiazolyl]formamide", *Cancer Biochem. Biophys.*, 1977, Vol. 2., pp 59–63. Exfoliated bladder cells obtained from rats similarly treated for much shorter periods of time which were insufficient to cause bladder cancer did not show the significant increase in galactosyl transferase.

Based upon this discovery that the level of a specific enzyme, galactosyl transferase, was significantly different in exfoliated cells from tissue containing cancerous cells than the level in comparable cells from normal tissue, an enzymatic noninvasive test for cancer in mammalian tissue was developed. This test is described in U.S. Pat. No. 4,132,600 issued to Plotkin et al. In the method described therein, exfoliated cells from tissue to be tested and assayed for the level of galactosyl transferase activity are incubated with an exogenous galactose acceptor, such as a modified glycoprotein, and a galactose-containing substrate, such as a nucleotide galactose sugar. The amount of galactose transferred by the enzyme in a given time under standard conditions to the acceptor can then be determined and is a measure of the level of galactosyl transferase activity present. If the activity is significantly different from normal values, the organ is likely to contain cancerous tissue.

The enzymatic noninvasive method for detecting cancer described in the Plotkin et al. patent has proven to be highly reliable. It would be an advantage, nevertheless, to have a more rapid, direct and/or inexpensive technique for detecting altered levels of galactosyl transferase.

DISCLOSURE OF THE INVENTION

This invention comprises an improved noninvasive method for detecting cancer in cells. This improved method comprises sensing for a specific label which is indicative of the amount of galactose moieties associated with the cells being tested.

In one embodiment, the improved method comprises the addition, to cells being tested, of a specific label which: (1) has a specific affinity for β-linked galactose moieties; and (2), once bound, can be directly detected because of its optical, electrical, magnetic, or other such properties or because it can be further reacted with materials having such directly detectable properties. Thus, an enzymatic transfer is not required and a rapid and inexpensive technique for screening a large number of test cells which are potentially cancerous is provided.

BEST MODE OF CARRYING OUT THE INVENTION

In the case of bladder cancer, it has been shown that there is an increased level of galactosyl transferase associated with the plasma membrane. This was demonstrated by culturing cells of transitional cell carcinoma line MGH-U1, in suspension, and then assaying them for galactosyl transferase by measurement of the transfer of [$^3$H]galactose from uridine diphosphate[$^3$H]galactose to desialylated ovine submaxillary mucin. The assay was optimized with respect to time and to protein, uridine diphosphate-galactose, desialylated ovine submaxillary mucin, and Triton X-100 concentrations. This assay was then applied to fresh specimens of benign, inflamed, and neoplastic bladder epithelium from 33 patients who underwent cold-cup biopsies at cystoscopy. Transitional cell carcinoma specimens gave values in the range of 24.7–184.8 cpm [$^3$H]galactose transferred/μg protein per hour (72.0±44.7, mean±S.D.M., n=25); normal and inflamed specimens ranged from 0.8–46.1 cpm/μg protein per hour (8.3±8.4, mean±S.D.M., n=35). By using a known method of cell rupture, cell ghosts, representing cell-surface membranes, were isolated both from the cultured cell line and from two biopsy specimens of transitional cell carcinoma, and the elevated galactosyl transferase was shown to be located in the cell-surface membrane fraction.

Thus, the improved method of this invention can be employed to detect increased levels of galactosyl transferase activity, which in turn is an indication of bladder cancer. This increased level of galactosyl transferase activity introduces β-linked galactose moieties into the plasma membrane of bladder cells, and these moieties can serve as binding sites for labels having a specific affinity for β-linked galactose moieties. The specific label should be one capable of being sensed.

A specific label having both properties (i.e., specific affinity and directly sensible) can be formed by reacting the lectin Ricinus Communis Agglutinin 120 (RCA$_{120}$), which is derived from Castor beans, with fluorescein, which is a fluorescent dye. This specific label is commercially available pre-reacted and can be purchased, for example, from Vector Laboratories, Inc., Burlingame, California.

Other lectins, in addition to RCA$_{120}$, can be employed as long as they have a specific affinity for β-galactose moieties. Lectins known to have such specific affinity and which are commercially available include peanut agglutinin (PNA) and Phaseolus Vulgaris Erythro-Agglutinin (PHA-E). Bandieraea Simplicifolia Lectin (BSL) has a specific affinity for α-linked galactose moieties, and is not satisfactory in the assay described herein. These lectins are also commercially available from Vector Laboratories.

Of the above-mentioned lectins, RCA$_{120}$ is the preferred lectin because of the very high specific affinity it displays for β-linked galactose moieties.

Similarly, other fluorescent dyes, in addition to fluorescein, can be employed. For example, all fluorescent dyes in the Rhodamine family could be used in place of fluorescein.

Further, the optically detectable property need not be fluorescence but might be another optical property detectable in some other manner. For example, dyes which produce a direct stain which is detectable could also be bound to a lectin specific for β-linked galactose moieties and employed with this invention.

A wide variety of assays employing $RCA_{120}$ bound to fluorescein ($RCA_{120}$-F) have actually been carried out. It has been found that this assay is highly reliable and significant fluorescence in the plasma membrane for all bladder cells known to be cancerous has been seen. On the other hand, no significant fluorescence has been detected for bladder cells known not to be cancerous.

Evidence seems to suggest that it is β-linked galactose moieties introduced by the increased presence of galactosyl transferase in the plasma membrane which is being detected, although this evidence is not conclusive. There are other possibilities, and one is that it is simply the increased level of the enzyme itself, which might be a glycoconjugate containing β-linked galactose moieties, which is being detected.

In any event, there is a striking difference between the fluorescence observed in the plasma membrane for cancerous bladder cells contrasted to the lack of any significant fluorescence in the plasma membrane of normal bladder cells.

One of the major advantages of the method described herein is that there is currently existing apparatus capable of detecting optical properties, such as fluorescence, employed with this method. For example, the Ortho Division of Johnson and Johnson produces a Cytofluorograph having this capability. Similarly, Becton & Dickinson markets a Fluorescence Activated Cell Sorter (FACS) and Coulter Systems markets a Cell Sorter, and both of these can be employed with this invention. Some of these, such as the Cytofluorograph, count the cells present in the sample by sensing scattered light from them while simultaneously counting the number of cells showing fluorescence. Typically, this data is obtained in a histogram which can be obtained in a very short time with a very small sample.

As those skilled in the art will understand, the sensing technique employed to detect the label need not be an optical technique. For example, it may be a ferromagnetic technique, such as nuclear magnetic resonance (NMR) or electron spin resonance (ESR) employed with a label involving ferritin, which has ferromagnetic properties, and which is attached to a compound having a specific affinity for the enzyme. The label may also be an enzymatic marker and may involve enzymes such as lacto-peroxidase, galactose-oxidase, horseradish peroxidase, etc. Such enzymes oxidize galactose which can then be reacted with a chromogen to produce a color.

Radiometric detection procedures are also suitable. For example, galactose moieties in the plasma membrane of cancerous bladder cells could be first oxidized and then labeled with tritium which could be sensed by detecting the radioactive counts produced by a sample.

Radioimmunoassay (RIA) techniques can also be used by employing an antibody coupled to a specific lectin in conjunction with labeled lectin.

Although the experimental work described herein is directed to the detection of bladder cancer, it is believed that other forms of cancer can be detected in human or other mammals by the method disclosed. In addition, although the method described herein can usually be employed in a noninvasive mode, it is within the scope of this invention to employ this assay coupled with an invasive method for obtaining the test cells.

This invention can be further and more specifically described by reference to the following examples.

Example 1

Incubation of Label with Slices of Rat Tumor and Normal Bladder Tissue

Frozen sections of tumor biopsies from cancerous rat bladder and normal rat bladder tissue were cut using a cryotome. The cancerous tumor was produced by a FANFT-induced AY27 tumor cell line injected into a healthy rat. The biopsies were first frozen in liquid nitrogen or dry ice-acetone, placed in the cryotome and directly cut to 10 μm slices. The need for paraffin imbedding was thus obviated.

The tumor and normal slices were subsequently washed and submerged in a solution of $RCA_{120}$-F in phosphate-buffered saline (PBS) for 10 minutes. The solution of specific label was prepared by dispersing 1 mg of $RCA_{120}$-F obtained from Vector Laboratories in 10 ml of 0.002 M phosphate-buffered saline (PBS), pH 7.2. Slices were removed from the solution, washed once again, and examined with a Leitz UV microscope. Striking fluorescence limited to the cell membrane was observed in the cancerous tissue whereas no fluorescence could be detected for the normal bladder tissue.

Example 2

Label Incubated with Rat Cell Lines Obtained From Bladder Tumor

The cancerous rat cell line of Example 1 was employed.

Cells were maintained as monolayer cultures in 35×10 mm falcon plastic Petri dishes with McCoy's 5A medium modification supplemented with 10% fetal calf serum and incubated in 95% air/5% $CO_2$ at 37° C. Cells were harvested near confluency by gentle trypsinization, washed, resuspended in 0.1 M MES, pH 6.5, and incubated.

Glass cover slips (Fisher 22×22 mm thickness number 1) were placed in a humidified chamber and cells in media were placed on these slides. Cells grew as monolayers over the slides. After a confluent layer had formed over the slides, the slides were washed lightly in PBS in a humidified chamber in 0.5 ml of PBS containing $RCA_{120}$-F, prepared as in Example 1, was placed over the slide and incubated for 10 minutes at 30° C. After the 10-minute incubation at 30° C., the slides were washed gently, again with PBS, and examined with a Leitz UV microscope equipped with bandpass filters for fluorescein. Striking fluorescence limited to the cell membrane was observed.

Example 3

Label Incubated with Slices of Kidney and Ureter

The procedures of Example 1 were employed except that the biopsies were taken from normal rat kidney and normal rat ureter. When the slices were examined with a Leitz UV microscope, no significant fluorescence could be detected.

Example 4

Label Incubated with Human Cell Lines

The procedures of Example 2 were used, except that human transitional cell carcinoma cell lines established from human urinary bladder carcinoma at the Massachusetts General Hospital, Boston, Mass., were employed. These were MGH-U1; MGH-U2; RT4; and T24. In addition, an established line derived from normal human urothelium and the established line MGH-316 derived from normal skin fibroblasts were also employed. Striking fluorescence, limited to the cell membrane, was observed in each tumor cell line, but no significant fluorescence was detected for the normal cell lines.

Example 5

Label Incubated with Human Biopsies

The procedures of Example 1 were employed except that frozen sections of twenty-one bladder tumor biopsies and four normal urothelial biopsies were cut using a cryotome.

Striking fluorescence, limited to the cell membrane, was observed for the cancerous cells, but no significant fluorescence was detected for the normal biopsies.

Example 6

Label Incubated with Human Urine

Urine samples were collected from human patients with and without transitional cell carcinoma. The urine samples were processed at about 20° C. and spun in a centrifuge at $1,000 \times g$. The pellets obtained were resuspended in PBS and respun to wash the exfoliated cells. The cells thus obtained were resuspended in PBS, placed on a cover slip and processed with $RCA_{120}$-F as described in Example 2. Upon examination under the Leitz UV microscope, the same striking fluorescence, limited to the cell membrane, was observed for cells from patients having transitional cell carcinoma, but no significant fluorescence was detected for cells from the urine of normal patients.

Example 7

Controls

Glucose, galactose, lactose and concanavalin A lectin were each preincubated at 1, 10 and 100 mM with RCA-F solution described in Example 4. Examples 4, 5 and 6 were then repeated as described.

Glucose had no effect on the results. Galactose and lactose (glucose-galactose) totally inhibited fluorescence at levels tested, presumably by binding to galactose moieties sensitive to RCA lectin. Concanavalin A had no effect on binding of RCA, since it is a lectin specific for glucose and mannose.

Example 8

For purposes of comparison, blind studies were made involving an assay for bladder cancer performed on the urine obtained from patients previously assayed for bladder cancer employing standard cytological procedures.

The methods employed in these blind studies were as follows.

Preparation of Urine Samples

1. Centrifuge urine ($1600 \times g$ to $3000 \times g$).
2. Discard supernatant.
3. Resuspend pellet in 4 ml of a buffer solution of 0.01 M $Na_2HPO_4$, 0.15 M NaCl and 0.01 M $Na_4$-EDTA, adjusted to a pH of 6.0 with HCl.
4. Layer sample on top of 3 ml of an isopycnic discontinuous density gradient.
5. Centrifuge at $400 \times g$ for 30 minutes.
6. Discard supernatant layer.
7. Separate interface layer from pellet layer.
8. Add above buffer solution to interface and pellet layers. Centrifuge at $1600 \times g$ for 10 minutes. Decant supernatants. Resuspend pellets in minimal volume of buffer.
9. Air-dry interface layer and pellet onto separate microscope slides.
10. Soak slides in acetone for 5 minutes.

Staining of Slides with Ricinus Communis Agglutinin Type I Bound to Fluorescein Isothiocyanate ($RCA_I$-FITC)

1. Mix 3.3 mg/ml $RCA_I$-FITC (Vector Labs) with above buffer, 1.0% nonionic detergent, and adjust to pH 6.0 with HCl. Mix so that each slide will receive approximately 3 microliters of $RCA_I$-FITC and 3 drops of buffer.
2. Apply 3 drops of mix to each slide. Cover slides with cover slips. Incubate in the dark for 10 minutes.
3. Wash cover slips off with buffer.
4. Soak slides in 200 ml buffer, pH 6.0, for about 20 minutes.
5. Remove slides from soak. Place 3 drops buffer, pH 6.0, onto each slide. Cover slides with cover slips.
6. Observe slides via fluorescence microscopy and look for green fluorescence on all cell surfaces.

Staining Slides with $RCA_I$-Biotin, Avidin-Horseradish Peroxidase, and Hanker-Yates Stain (Polysciences, Inc.)

1. Mix 3.5 mg/ml $RCA_I$-Biotin (Vector Labs) with buffer, pH 6.0, and 1.0% nonionic detergent so that each slide receives approximately 5 microliters $RCA_I$-Biotin and 3 drops buffer. Cover slides with cover slips. Incubate 10 minutes. Wash cover slips off. Soak slides in buffer, pH 6.0, for 20 minutes. Remove from soak.
2. Mix 3.6 mg/ml Avidin-HRP (Vector Labs) with buffer, pH 6.0, and 1.0% nonionic detergent so that each slide receives approximately 5 microliters Avidin-HRP and 3 drops buffer. Cover slides with cover slips. Incubate 20 minutes. Wash cover slips off. Soak slides in buffer, pH 6.0, for 20 minutes. Remove from soak.
3. Make developer solution:
Mix 5 milligrams Hanker-Yates developer with 10 ml PBS+1.0% nonionic detergent, pH 7.4 via HCl. Add 0.1 ml of a 1.0% $H_2O_2$ (hydrogen peroxide) solution (made with distilled water). Mix well.
4. Apply Hanker-Yates developer solution to slides. Solution is applied until slides are completely covered. Incubate 10 minutes. Pour off developer. Soak in PBS, pH 7.4, for 20 minutes. Remove from soak. Apply 3 drops PBS, pH 7.4, per slide. Cover with cover slips. Observe via visible light microscopy.
5. Look for cells which have stained medium to dark brown.

Cytological Procedures

A commercially available Papanicolaou stain was employed after centrifuging the urine and smearing the pellet onto glass slides.

The smears were observed for:
1. Enlargement of cell nucleus.
2. Hyperchromasia (cell nucleus stains more heavily than in a normal cell).
3. Microscopic hematuria.
4. Occasional leucocytes (white blood cells).
5. Cell nuclei are irregular.
6. Abnormal chromatin patterns (chromatin=stainable nuclear cytoplasm).
7. Enlargement of cells, scanty cytoplasm.

In these comparative blind tests, there was correspondence in the results obtained between the cytological and assay conclusions with regard to bladder cancer in 28 out of 37 cases (75.7%).

The assay produced:

| | |
|---|---|
| One False Negative: | Grade I Bladder Tumor |
| Eight False Positives: | 1 post resection bladder cancer |
| | 1 cured bladder cancer |
| | 1 prostate cancer |
| | 1 prostate cancer - post prostatectomy urine sample |
| | 1 renal cancer - post nephrectomy urine sample |
| | 1 bladder calculi |
| | 1 chronic cystitis |
| | 1 hematuria. |

INDUSTRIAL APPLICABILITY

The method described herein is useful in assaying for galactose moieties and provides a noninvasive test for cancer in tissue from mammals, including humans.

EQUIVALENTS

Those skilled in the art will recognize, or be able to ascertain using no more than routine experimentation, many equivalents to the specific embodiments to the invention described herein. Such equivalents are intended to be encompassed by the following claims.

We claim:

1. A method for determining whether mammalian tissue cells are malignant, comprising:
   (a) adding to said cells a label which (1) has a specific affinity for $\beta$-linked galactose moieties, and (2) can be detected;
   (b) thereafter, detecting the amount of said label bound to said cells or components thereof.

2. The method of claim 1 wherein said label comprises a lectin coupled to a fluorescent dye.

3. The method of claim 2 wherein said lectin comprises $RCA_{120}$.

4. The method of claim 3 wherein said dye comprises fluorescein.

5. An improved noninvasive test for cancer in mammals, comprising:
   (a) incubating cells from said mammalian tissue in the presence of a label which: (1) has a specific affinity for $\beta$-linked galactose moieties present in the membrane of said cells; and, (2) is capable of being detected after it becomes bound to said $\beta$-linked galactose moieties in said cell membrane;
   (b) detecting the amount of said label which is bound to said cell membrane; and,
   (c) comparing the amount of said label bound to the cell membrane of test cells to the level which would be present in non-cancer cells.

6. A test of claim 5 wherein said label comprises a lectin bound to a dye.

7. A test of claim 6 wherein said dye is a fluorescent dye.

8. A test of claim 7 wherein said lectin comprises $RCA_{120}$.

9. A test of claim 8 wherein said dye comprises fluorescein.

10. A method for determining whether mammalian cells are cancerous comprising determining the level of $\beta$-linked galactose moieties associated with the plasma membrane of said cells and comparing the level found with the level associated with non-cancerous cells.

11. A method of claim 10 wherein said level of $\beta$-linked galactose moieties is determined by an optical technique.

12. An assay for detecting $\beta$-linked galactose moieties on, within or shed from cells comprising contacting said cells with a label which (1) has a specific affinity for $\beta$-linked galactose moieties and (2) is capable of being sensed after it becomes bound to said moieties and thereafter sensing for said label.

* * * * *